United States Patent [19]

Baker et al.

[11] Patent Number: 6,071,856
[45] Date of Patent: Jun. 6, 2000

[54] HERBICIDAL COMPOSITIONS FOR ACETOCHLOR IN RICE

[75] Inventors: Don R. Baker, Orinda; Richard L. Franz, Pt. Richmond; Khosro Khodayari, Walnut Creek, all of Calif.

[73] Assignee: Zeneca Limited, London, United Kingdom

[21] Appl. No.: 08/812,953

[22] Filed: Mar. 4, 1997

[51] Int. Cl.[7] .............................. A01N 25/32; A01N 37/22
[52] U.S. Cl. ....................... 504/110; 504/105; 504/109; 504/341; 504/342
[58] Field of Search ................................... 504/110, 105, 504/109, 341, 342

[56] References Cited

U.S. PATENT DOCUMENTS

| | | | |
|---|---|---|---|
| 4,199,506 | 4/1980 | Howe et al. | 548/201 |
| 4,437,876 | 3/1984 | Howe et al. | 504/106 |
| 4,818,270 | 4/1989 | Grabiak et al. | 504/105 |
| 4,964,893 | 10/1990 | Brannigan et al. | 504/100 |
| 5,256,626 | 10/1993 | Williams et al. | 504/107 |
| 5,502,025 | 3/1996 | Bussler | 504/107 |

FOREIGN PATENT DOCUMENTS 1064986   3/1992   China .

*Primary Examiner*—John Pak
*Attorney, Agent, or Firm*—Dianne Burkhard

[57] ABSTRACT

This invention is directed to an herbicidal composition comprising, a) an herbicidally effective amount of acetochlor; and
b) a non-phytotoxic antidotally effective amount of a compound according to formula (I),

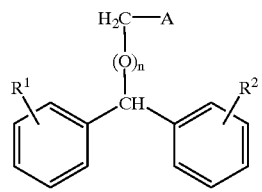

(I)

wherein each of $R^1$ and $R^2$ independently represents one or more substituents selected from hydrogen, $(C_1-C_6)$alkyl, $(C_1-C_6)$alkoxy, $(C_1-C_6)$alkylamino, halo, halo$(C_1-C_6)$alkyl, $(C_1-C_6)$alkoxy-$(C_1-C_6)$alkyl and nitro;

wherein A is selected from

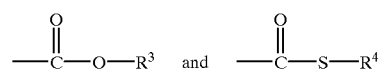

wherein each of $R^3$ and $R^4$ is independently selected from hydrogen, $(C_1-C_6)$alkyl, halo$(C_1-C_6)$alkyl, cyano$(C_1-C_6)$alkyl, $(C_1-C_6)$alkoxy-$(C_1-C_6)$alkyl, $(C_2-C_6)$alkenyl, $(C_2-C_6)$alkynyl, phenyl, nitrophenyl, benzyl, halobenzyl, pyridinyl$(C_1-C_6)$alkyl and $(C_1-C_6)$alkylammonium; and n is 0 or 1.

9 Claims, No Drawings

HERBICIDAL COMPOSITIONS FOR ACETOCHLOR IN RICE

FIELD OF THE INVENTION

This invention relates to safeners, herbicide compositions and methods of their use and more particularly, to safened acetochlor compositions and their use on rice.

BACKGROUND OF THE INVENTION

The need for effective herbicides needs no special emphasis. The control of weeds and undesirable vegetation is of great economic importance since weed competition inhibits the production of foliage, fruit or seed and agricultural crops. The presence of weeds can reduce harvesting efficiency and the quality of the harvested crop. Thus, suppression of undesirable weed growth is very advantageous.

Herbicides are generally used to control or eradicate weed pests on a variety of crops. The particular emphasis of the instant invention is the suppression of undesirable weeds at the locus of rice plants. Herbicides are useful because they increase rice yields and reduce harvest costs.

Some herbicides may injure rice plants at application rates necessary to control weed growth. To be effective, an herbicide must cause at most minimal damage to the rice plant while maximizing injury to weed species which infest the locus of the rice plant. To preserve the beneficial aspects of herbicides which injure plants beyond acceptable levels, many herbicide safeners have been prepared. These safeners reduce or eliminate damage to the rice plant without substantially impairing the damaging effect of the herbicide on weed species.

U.S. Pat. No. 4,964,893 ("Brannigan et al.") incorporated herein by reference, discloses certain benzhydryl compounds as effective safeners for a variety of herbicides. These herbicides include thiocarbamates, triazines, diphenylethers, benzoic acid derivatives, phenyl ureas and acetamides. Brannigan et al. also disclose that the combination of one or more of the foregoing herbicides with one or more of the safeners disclosed therein is effective for the control of weeds with concomitant low crop injury. These crops include corn, grain sorghum, and cereals such as wheat, rice, barley, oats a rye as well as soybeans and cotton.

However, as is outlined in *Crop Safeners for Herbicides*, ed. by K. K. Hatzios and R. E. Hoagland, Academic Press, San Diego, 1989, "[a]ll the presently available safeners exhibit a high degree of botanical and chemical specificity and protect only certain crops against injury from selected groups of herbicides." Id. at 66.

Thus, it appears that Brannigan et al. is overly broad in its determination of what combinations of herbicide and safeners will be effective in view of what is known in the art.

In general, safening activity is determined empirically by observing the complex interaction of several factors. Some of these factors include the interaction of the herbicide compound, the type of weed to be controlled, the crop to be protected, and the safening compound itself.

The herbicide used in the present invention is 2-chloro-N-(ethoxymethyl)-6'-ethyl-o-acetotoluidide. It has the common name acetochlor and has the following chemical structural formula:

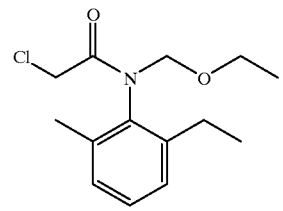

A particularly effective class of safening compounds with use of acetochlor are of the formula

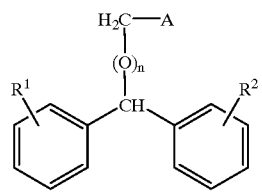

(I)

wherein each of $R^1$ and $R^2$ independently represents one or more substituents selected from hydrogen, alkyl, alkoxy, alkylamino, halo, haloalkyl and nitro; wherein A is selected from

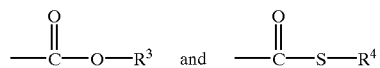

wherein each of $R^3$ and $R^4$ is independently selected from hydrogen, alkyl, haloalkyl, cyanoalkyl, alkenyl, alkynyl, phenyl, nitrophenyl, benzyl, halobenzyl, pyridinylalkyl and alkylammonium; and n is 0 or 1.

The safening of acetochlor for some crop species is known in the art. In fact, Brannigan et al. disclose acetochlor safening with some of the safeners above in sorghum, corn and soybean. In addition, the same patent discloses a well known herbicide, butachlor, 2-chloro-2',6'-diethyl-N-(butoxymethyl) acetanilide, use on rice with an appropriate safener. However, the use of acetochlor on rice plants is not disclosed.

The compounds disclosed herein have been found to be especially useful for safening rice against injury caused by acetochlor. As discussed more fully below, rice may be grown or cultured using a variety of methods. The following is a description of different rice culturing methods:

In the postflood postemergence (transplanted) method, rice is grown to the 2–4 leaf stage away from the field. The field is flooded and tilled (puddled) until a blend of mud is achieved. The rice plants are then transplanted into this mud. Herbicide application typically takes place before or after flooding.

In the postflood postemergence (water seeded) method, rice is soaked for 24 or more hours, then is sown to the surface of a shallow flooded field. Herbicide application is typically after weed germination.

In the preflood postemergence direct seeded (broadcast or drilled) method, rice is broadcasted or planted with a planter under the soil surface. The field may be flushed (watered) to promote rice growth. The field is flooded 1 week or more after this planting as the plants germinate. Herbicide application takes place typically before this flood, but after emergence of the rice plants.

In the preflood postemergence (South East Asia style) method, rice is soaked for 24 or more hours. The field is puddled to the right consistency and drained. The pre-germinated seeds are then broadcast to the surface of the soil. Flooding takes place as the rice develops. Herbicide application normally takes place before the flooding, but after the emergence of the rice plants.

Finally, in the preemergence or delayed preemergence method, seeds are planted usually with a planter of sorts. Herbicide application is made before emergence of the rice or weeds.

In China, acetochlor has been applied for weed control in rice in a postflood, postemergence application at very low concentration levels of active ingredient. However, this use has not produced good results because no safener is employed and thus the rice plants suffer phytotoxic effects.

Although the use of acetochlor on other crop species is known, it was thought to be too injurious to rice at the concentration levels necessary for effective weed suppression. Surprisingly, the inventors have found that acetochlor may be used on rice plants at effective levels when a safener is employed. High levels of weed control are possible with acetochlor and with the appropriate safener, rice injury is reduced to an acceptable level.

SUMMARY OF THE INVENTION

In one aspect, this invention is directed to an herbicidal composition comprising, a) an herbicidally effective amount of acetochlor; and
b) a non-phytotoxic antidotally effective amount of a compound according to formula (I),

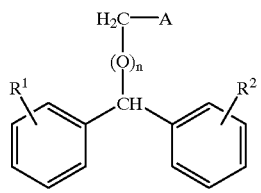

(I)

wherein each of $R^1$ and $R^2$ independently represents one or more substituents selected from hydrogen, $(C_1-C_6)$alkyl, $(C_1-C_6)$alkoxy, $(C_1-C_6)$alkylamino, halo, halo$(C_1-C_6)$alkyl, $(C_1-C_6)$alkoxy-$(C_1-C_6)$alkyl and nitro;

wherein A is selected from

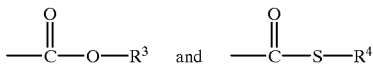

wherein each of $R^3$ and $R^4$ is independently selected from hydrogen, $(C_1-C_6)$alkyl, halo$(C_1-C_6)$alkyl, cyano$(C_1-C_6)$alkyl, $(C_1-C_6)$alkoxy-$(C_1-C_6)$alkyl, $(C_2-C_6)$alkenyl, $(C_2-C_6)$alkynyl, phenyl, nitrophenyl, benzyl, halobenzyl, pyridinyl$(C_1-C_6)$ alkyl and $(C_1-C_6)$alkylammonium; and n is 0 or 1.

In another aspect, this invention is directed to a method for reducing injury to a rice plant, said injury due to acetochlor, comprising applying to an area of the plant locus a non-phytotoxic antidotally effective amount of a compound of formula (I),

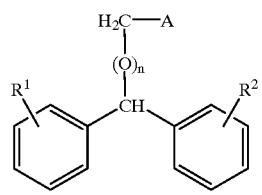

(I)

wherein:
$R^1$, $R^2$, $R^3$, $R^4$, A and n are as defined above.

DETAILED DESCRIPTION OF THE INVENTION

In one aspect, this invention is directed to an herbicidal composition comprising, a) an herbicidally effective amount of acetochlor; and
b) a non-phytotoxic antidotally effective amount of a compound according to formula (I),

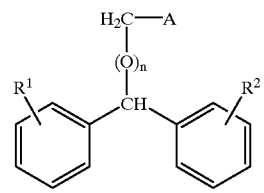

wherein each of $R^1$ and $R^2$ independently represents one or more substituents selected from hydrogen, $(C_1-C_6)$alkyl, $(C_1-C_6)$alkoxy, $(C_1-C_6)$alkylamino, halo, halo$(C_1-C_6)$alkyl, $(C_1-C_6)$alkoxy-$(C_1-C_6)$alkyl and nitro;

wherein A is selected from

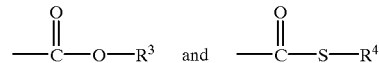

wherein each of $R^3$ and $R^4$ is independently selected from hydrogen, $(C_1-C_6)$alkyl, halo$(C_1-C_6)$alkyl, cyano$(C_1-C_6)$alkyl, $(C_1-C_6)$alkoxy-$(C_1-C_6)$alkyl, $(C_2-C_6)$alkenyl, $(C_2-C_6)$alkynyl, phenyl, nitrophenyl, benzyl, halobenzyl, pyridinyl$(C_1-C_6)$ alkyl and $(C_1-C_6)$alkylammonium; and n is 0 or 1.

More particularly preferred compounds within formula I are those wherein each of $R^3$ and $R^4$ is independently selected from hydrogen, methyl, ethyl, 1-methylethyl, 1,1-dimethylethyl, n-propyl, 2-propenyl, 1-methyl-2-propynyl, 1-ethyl-2-propynyl, 2,2,2-trifluoroethyl, 1-methyl-2,2,2-trifluoroethyl, 2,2,3,3-tetrafluoropropyl, 2-cyanoethyl, 2-cyano-1-methylethyl, phenyl, 3-nitrophenyl, benzyl, 4-chlorobenzyl, 3-pyridinylmethyl, and 1,1-dimethylethylammonium, and wherein each of $R^1$ and $R^2$ represents substituents independently selected from hydrogen, 2-methyl, 2,6-dimethyl, 4-chloro, 2-trifluoromethyl, 3-trifluoromethyl and 5-trifluoromethyl.

The most preferred safeners are 3,3-diphenylpropionic acid (compound 1, Table I) benzhydryloxyacetic acid (compound 2, Table I); and methyl benzhydryloxy acetate (compound 3, Table I).

In another aspect, this invention is directed to a method for reducing injury to a rice plant, said injury due to acetochlor, comprising applying to an area of the plant and/or locus thereof a non-phytotoxic antidotally effective amount of a compound of formula (I),

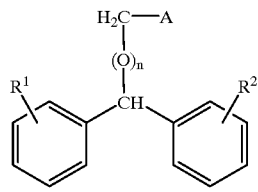

wherein: $R^1$, $R^2$, $R^3$, $R^4$, A and n are as defined above.

The formulae given above are intended to include any physically distinguishable modifications of the compounds which may arise, for example, from different ways in which the molecules are arranged in a crystal lattice, or from the inability of parts of the molecule to rotate freely in relation to other parts, or from geometrical isomerism, or from intramolecular or intermolecular hydrogen bonding, or otherwise. As employed herein, the word "halogen" includes fluoro, chloro, bromo and iodo groups.

The terms "herbicide" and "herbicidal" are used herein to denote the inhibitive control or modification of undesired plant growth. Inhibitive control and modification include all deviations from natural development, such as total killing, growth retardation, defoliation, desiccation, regulation, stunting, tillering, stimulation, leaf burn and dwarfing. The term "herbicidally effective amount" is used to denote any amount which achieves such control or modification when applied to the undesired plants themselves or to the area in which these plants are growing. The term "plants" is intended to include germinated seeds, emerging seedlings and established vegetation, including both roots and above-ground portions.

The terms "antidote", "safening agent", "safener", "antagonistic agent", "interferant", "crop protectant" and "crop protective", are often-used terms denoting a compound capable of reducing the phytotoxicity of a herbicide to a crop plant or crop seed. The terms "crop protectant" and "crop protective" are sometimes used to denote an herbicide-safener combination which provides protection from competitive weed growth by reducing herbicidal injury to a valuable crop plant while at the same time controlling or suppressing weed growth occurring in the presence of the crop plant. An "antidotally effective amount" of an antidote or safener is that amount which protects crop plants by interfering with the herbicidal action of a herbicide on the crop plants, but without interfering with the herbicidal action on weeds, so as to render the herbicide selective to weed plants emerging or growing in the presence of crop plants.

The safener is applied in conjunction with acetochlor in a non-phytotoxic antidotally effective amount. By "non-phytotoxic" is meant an amount which causes at most minor or no injury to the desired rice plant. The preferred weight ratio of acetochlor to safener is from about 0.1:1 to about 30:1. An even more preferred weight ratio range is from about 2:1 to about 2:5.

The compounds of formula I may be generated by reacting a substituted benzhydrol with an equivalent amount (or slight excess) of an alkyl bromoacetate (example methyl bromoacetate $BrCH_2CO_2CH_3$) in the presence of a base (between 1–2 equivalents) to produce a compound of formula I wherein $R^1$, $R^2$, $R^3$, $R^4$, A and n are as defined above. A suitable base is sodium hydride.

Additional procedures to synthesize compounds of formula I are outlined in U.S. Pat. No. 4,964,893.

FORMULATIONS

A formulation is the incorporation of a formulant in a form which is directly usable on crops and weeds. As defined herein, a "formulant" is the material which is to be formulated. The formulant may be either an antidote compound alone or an herbicide and antidote composition. The purpose of the formulation is to apply the formulant to the locus of a crop where it is desired to establish herbicidal selectivity by a convenient method. The "locus" may include soil, seeds, crop, crop seeds, seedlings and vegetation.

The antidotes described herein can be formulated in a number of ways for suitable application: (a) the antidote can be formulated for application directly to the crop seed; (b) the antidote and herbicide may be formulated separately and applied separately or applied simultaneously in an appropriate weight ratio, e.g., as a tank mix, or (c) the antidote and herbicide may be formulated together in the proper weight ratio.

The choice of formulation and mode of application for any given composition may affect its activity, and selection will be made accordingly. The composition of the invention may thus be formulated as wettable powders, as emulsifiable concentrates, as powders or dusts, as flowables, as solutions, suspensions or emulsions, granules or in controlled-release forms such as microcapsules. These formulations may contain as little as about 0.5% to as much as about 95% or more by weight of active ingredient. The optimum amount for any given composition will depend upon the species of rice and its environment. The rate of application will generally vary from about 0.01 to about 11.5 kilograms per hectare, preferably from about 0.02 to about 4.5 kilograms per hectare.

Wettable powders are in the form of finely divided particles which disperse readily in water or other liquid carriers. The particles contain the active ingredient retained in a solid matrix. Typical solid matrices include fuller's earth, kaolin clays, silicas and other readily wettable organic or inorganic solids. Wettable powders normally contain about 5% to about 95% of the active ingredient plus a small amount of wetting, dispersing, or emulsifying agent.

Emulsifiable concentrates are homogeneous liquid compositions dispersible in water or other liquid, and may consist entirely of the active compound with a liquid or solid emulsifying agent, or may also contain a liquid carrier, such as xylene, heavy aromatic naphthas, isophorone and other nonvolatile organic solvents. In use, these concentrates are dispersed in water or other liquid and normally applied as a spray to the area to be treated. The amount of active ingredient may range from about 0.5% to about 95% of the concentrate.

Dusts are free-flowing admixtures of the active ingredient with finely divided solids such as talc, clays, flours and other organic and inorganic solids which act as dispersants and carriers.

Granules are in the form of small pellets of clay or other matrix designed to sink to the bottom of a flooded field then release the active ingredient.

Microcapsules are typically droplets or solutions of the active material enclosed in an inert porous shell which allows escape of the enclosed material to the surrounds at controlled rates. Encapsulated droplets are typically about 1 to 50 microns in diameter. The enclosed material typically constitutes about 50 to 95% of the weight of the capsule, and may include solvent in addition to the active compound. Shell of membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for herbicidal applications include simple solutions of the active ingredient in a solvent in which it is completely soluble at the desired concentration, such as water, acetone, alkylated naphthalenes, xylene and other organic solvents. Pressurized sprayers, wherein the active ingredient is dispersed in finely-divided form as a result of vaporization of a low boiling dispersant solvent carrier may also be used.

Many of these formulations include wetting, dispersing or emulsifying agents. Examples are alkyl and alkylaryl sulfonates and sulfates and their salts; polyhydric alcohols; polyethoxylated alcohols; esters and fatty amines. These agents when used normally comprise from 0.1% to 15% by weight of the formulation.

Each of the above formulations can be prepared as a package containing the herbicide together with other ingredients of the formulation (diluents, emulsifiers, safeners, surfactants, etc.). In addition, the herbicide and safener may be individually formulated. The formulations can also be prepared by a tank mix method, in which the ingredients are obtained separately and combined at the grower site.

EXAMPLES

The following examples are intended to further illustrate the present invention and are not intended to limit the scope of this invention in any manner whatsoever.

Example I
Methyl Benzhydryloxy Acetate (Compound 3, Table I).

To a 200 mL round bottom flask was added 0.7 grams of sodium hydride (0.023 mol, 80% in oil), 5 mL of tetrahydrofuran and 3.7 grams of benzhydrol (0.02 mol. dissolved in 20 mL of tetrahydrofuran) and the reaction mixture was refluxed for 5 minutes. Next, 2.1 mL of methyl bromoacetate (0.022 mol.) was added and a precipitate formed. The solvent was removed and the solid was dissolved in methylene chloride and water was added. The organic layer was removed and subsequently dried with magnesium sulfate. The resulting oil was chromatographed on a silica gel column using hexanes and ethylacetate. The product was confirmed by NMR, IR and mass spectrometry.

The compounds in Table I are effective safeners of acetochlor on rice. The syntheses of compounds 2 and 3 are described in U.S. Pat. No. 4,964,893.

TABLE 1

| Comp. No. | $R^1$ | $R^2$ | $R^3$ | n |
|---|---|---|---|---|
| 1 | H | H | H | 0 |
| 2 | H | H | H | 1 |
| 3 | H | H | $CH_3$ | 1 |

HERBICIDAL SCREENING TESTS

The compounds listed in the foregoing Table I were tested for herbicidal activity by the method below and at various rates of application. The results of some of these tests are given below. Results obtained in herbicidal screening are affected by a number of factors including: the amount of sunlight, soil type, soil pH, soil organic matter, temperature, humidity, depth of planting, plant growth stage, application method, application rate as well as many other factors. All testing procedures are administered with the least amount of variability possible. State of the art equipment and techniques are employed to enable the screening process to remain consistent and reliable.

PRE FLOOD POST EMERGENCE HERBICIDAL SCREENING TEST

Seeds of *Echinochloa crus-galli* ("ECHCG") were seeded ½ centimeter (cm) deep into 8.9×8.9 cm pots. The pots were previously filled with puddled clay soil which contained 2.2% organic matter and a pH of 5.7. In addition, the rice hybrid "Kaybonnet" (*Orysa Sativa*) was also seeded in pots to a depth of 1 cm.

The pots were placed into 10 liter plastic tubs lined with plastic bags. The tubs were sprayed with the test material in acetone/water 50:50 with 0.5% Tween 20® (a surfactant) at a rate of 200 grams acetochlor/ha and 500 grams/ha safener at the growth stages of 2–3 leaf both rice and ECHCG. The tubs were flooded with water to a depth of 2–3 cm 7 days after application The degree of rice phytotoxicity was evaluated and recorded 7 days after treatment (DAT) and compared to the growth of the rice plants of the same age in an untreated control flat. In addition, the degree of weed control/rice phytotoxicity was evaluated and recorded 28 DAT as a percentage of control as compared to the growth of the same species of the same age in an untreated control flat.

Percent control is the total injury to the plants due to all factors including: inhibited emergence, stunting, malformation, albinism, chlorosis, mecrosis and other types of plant injury. The control ratings range from 0 to 100 percent, where 0 represents no effect with growth equal to the untreated control and where 100 represents complete kill. Representative results are shown in Table II.

TABLE II

| | PRE-FLOOD POST EMERGENCE | | |
|---|---|---|---|
| COMP. NO. | RICE 7 DAT | RICE 28 DAT | ECHCG 28 DAT |
| 1 | 0 | 0 | 0 |
| 2 | 0 | 0 | 0 |
| 3 | 0 | 0 | 0 |
| acetochlor | 55 | 44 | 100 |
| 1 + acetochlor | 13 | 24 | 100 |
| 2 + acetochlor | 0 | 3 | 100 |
| 3 + acetochlor | 7 | 30 | 100 |

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

What is claimed is:

1. An herbicidal composition comprising,
   a) an herbicidally effective amount of acetochlor; and
   b) a non-phytotoxic antidotally effective amount of a compound according to formula Ia,

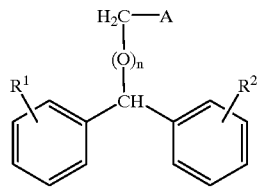

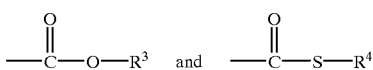

wherein each of $R^1$ and $R^2$ independently represents one or more substituents selected from the group consisting of hydrogen, $(C_1-C_6)$ alkyl, $(C_1-C_6)$ alkoxy, $(C_1-C_6)$ alkylamino, halo, halo$(C_1-C_6)$ alkyl, $(C_1-C_6)$alkoxy-$(C_1-C_6)$alkyl, and nitro; wherein A is selected from the group consisting of wherein each of $R^3$ and $R^4$ is independently selected from the group consisting of hydrogen, $(C_1-C_6)$ alkyl, halo$(C_1-C_6)$ alkyl, cyano$(C_1-C_6)$ alkyl, $(C_1-C_6)$alkoxy-$(C_1-C_6)$alkyl, $(C_2-C_6)$ alkenyl, $(C_2-C_6)$ alkynyl, phenyl, nitrophenyl, benzyl, halobenzyl, pyridinyl$(C_1-C_6)$alkyl and $(C_1-C_6)$ alkylammonium; and n is 0.

2. An herbicidal composition according to claim 1, wherein $R^3$ is hydrogen.

3. An herbicidal composition according to claim 1, wherein $R^3$ is $C_1-C_6$ alkyl.

4. An herbicidal composition according to claim 1, wherein $R^1$ is hydrogen; $R^2$ is hydrogen; and $R^3$ is hydrogen.

5. A method for reducing injury to a rice plant, said injury due to acetochlor, comprising applying to an area of the plant and/or locus thereof a) an herbicidally effective amount of acetochlor; and b) a non-phytotoxic antidotally effective amount of a compound according to formula Ib,

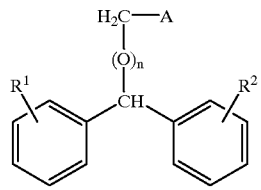

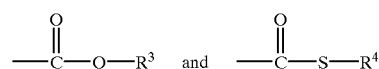

wherein each of $R^1$ and $R^2$ independently represents one or more substituents selected from the group consisting of hydrogen, $(C_1-C_6)$ alkyl, $(C_1-C_6)$ alkoxy, $(C_1-C_6)$ alkylamino, halo, halo$(C_1-C_6)$ alkyl, $(C_1-C_6)$alkoxy-$(C_1-C_6)$alkyl, and nitro; wherein A is selected from the group consisting of wherein each of $R^3$ and $R^4$ is independently selected from the group consisting of hydrogen, $(C_1-C_6)$ alkyl, halo$(C_1-C_6)$ alkyl, cyano$(C_1-C_6)$ alkyl, $(C_1-C_6)$alkoxy-$(C_1-C_6)$alkyl, $(C_2-C_6)$ alkenyl, $(C_2-C_6)$ alkynyl, phenyl, nitrophenyl, benzyl, halobenzyl, pyridinyl$(C_1-C_6)$alkyl and $(C_1-C_6)$ alkylammonium; and n is 0.

6. A method for reducing injury to a rice plant according to claim 1 wherein at least one of $R^1$, $R^2$, and $R^3$ is hydrogen.

7. A method for reducing injury to a rice plant according to claim 1 wherein at least one of $R^1$, $R^2$, and $R^3$ is $C_1-C_6$ alkyl.

8. A method for reducing injury to a rice plant according to claim 1 wherein $R^1$ is hydrogen; $R^2$ is hydrogen; and $R^3$ is hydrogen.

9. A method for reducing injury to a rice plant according to claim 1 wherein $R^1$ is hydrogen; $R^2$ is hydrogen; and $R^3$ is methyl.

* * * * *